US007736661B1

(12) United States Patent
Menon

(10) Patent No.: US 7,736,661 B1
(45) Date of Patent: Jun. 15, 2010

(54) METHOD OF TREATING SKIN CONDITIONS

(75) Inventor: Gopinathan K. Menon, Wayne, NJ (US)

(73) Assignee: Avon Products, Inc, New York, NY (US)

( * ) Notice: Subject to any disclaimer, the term of this patent is extended or adjusted under 35 U.S.C. 154(b) by 0 days.

(21) Appl. No.: 09/521,442

(22) Filed: Mar. 7, 2000

(51) Int. Cl.
*A61K 8/02* (2006.01)

(52) U.S. Cl. .................................................. 424/401

(58) Field of Classification Search ................ 424/401, 424/70.1, 70.03, 523, 72.5, 74.5, 484, 485, 424/725, 745; 514/859, 860; 426/401
See application file for complete search history.

(56) References Cited

U.S. PATENT DOCUMENTS

| 4,006,218 A | * | 2/1977 | Sipos | ........................... | 424/54 |
| 4,537,776 A | * | 8/1985 | Cooper | ....................... | 514/424 |
| 4,560,555 A | * | 12/1985 | Snider | ........................ | 424/78 |
| 4,986,983 A | | 1/1991 | Gerstein | | |
| 5,032,408 A | | 7/1991 | Schreuder | | |
| 5,162,377 A | | 11/1992 | Kakoki et al. | | |
| 5,252,333 A | | 10/1993 | Horrobin | | |
| 5,312,834 A | * | 5/1994 | Yeo | ............................ | 514/560 |
| 5,422,115 A | | 6/1995 | Horrobin | | |
| 5,445,822 A | * | 8/1995 | Bracco | ....................... | 424/401 |
| 5,705,170 A | * | 1/1998 | Kong et al. | ................. | 424/401 |
| 5,882,664 A | * | 3/1999 | Soma et al. | ................. | 424/401 |
| 5,939,442 A | | 8/1999 | Evans et al. | | |
| 5,945,109 A | * | 8/1999 | Schmidt et al. | ............. | 424/401 |
| 5,976,555 A | | 11/1999 | Liu et al. | | |
| 5,981,586 A | | 11/1999 | Pershadsingh | | |
| 5,994,554 A | | 11/1999 | Kliewer et al. | | |
| 5,997,852 A | | 12/1999 | Yoneda et al. | | |
| 6,004,751 A | * | 12/1999 | Rosenfield | ..................... | 435/6 |
| 6,284,268 B1 | * | 9/2001 | Mishra et al. | ............... | 424/455 |
| 2001/0041708 A1 | | 11/2001 | Halvorsen et al. | | |

FOREIGN PATENT DOCUMENTS

| EP | 0 203 211 | | 12/1986 |
| EP | 1 163 905 | | 12/2001 |
| JP | 03294215 | | 12/1991 |
| JP | 2884466 | | 12/1993 |
| JP | 3513861 | | 10/1994 |
| JP | 07145032 | | 6/1995 |
| JP | 07145032 A | | 6/1995 |
| JP | 07145034 A | | 6/1995 |
| JP | 08119829 | * | 5/1996 |
| JP | 03294215 A | | 12/2000 |
| WO | WO 99/49839 | | 10/1999 |
| WO | WO 00/53176 | * | 2/2000 |

OTHER PUBLICATIONS

Merriam Webster's Collegiate Dictionary, Tenth Edition, p. 184 and p. 1164. 1997.*
Abstract of Japanese Patent 7-187989 to Nagase Sangyo KK (NAGS). 1995.*
Abstract of Japanese Patent 8-119829 to Kose Corporation. 1996.*
Cellulite: A Review Article of Its Physiology and Treatment, Journal of Cosmetic and Laser Therapy, vol. 6, 2004 (Abstract).*
An assessment of traditional and Novel Therapies , Journal of Cosmetic and Laser Therapy, vol. 7, 2005 (Abstract).*
Terranova, F. et al "Cellulite: nature and aetiopathogenesis" International Journal of Cosmetic Science (2006) 28, p. 157-167.*
Zoe Diana Draelos "The Disease of Cellulite", Journal of Cosmetic Dermatology (Dec. 2005) 4, p. 221-222.*
Olszewski et al (1998) Clinical and Experimental Allergy, "Food Allergy to peanuts in France-evaluation of 142 observations" vol. 28, No. 7, p. 850-859.*
Moneret-Vautrin et al (1998) Clinical and Experimental Allergy, "Isolation and characterization of proteic allergens in refined peanut oil" vol. 28, No. 9, p. 1113-1119.*
Okuno et al "Perilla oil prevents the excessive growth of visceral adipose tissue in rats by down regulating adipocyte differentiation", J, Nutr. 127; (1997) p. 1752-1757.*
"Perilla oil" from wikipedia (http://en.wikipedia.org/wiki/Perilla_oil).*
"Orphan Nuclear Receptors: Shifting Endocrinology Into Reverse", By Steven A. Kliewer, Jürgen M. Lehmann, Timothy M. Wilson, pp. 757-780.
"Estrogrogen-induced Production of a Peroxisome Proliferator-activated Receptor (PPAR) Ligand in a PPARy-expressing Tissue" by Hongwen Ma, Howard W. Sprecher and Pappachan E. Kolattukudy, pp. 30131-30138.
European Search Report dated Apr. 29, 2003, European Patent Application No. 01914687.7.
Draelos, D. & Marenus, K.; Cellulite Biology and Purported Treatment; Dermatologic Surgery; Dec. 1997, p. 1177-1181, vol. 23, No. 12.
Rosen E. & Spiegelman, B.; Adipocytes as regulators of energy balance and glucose homeostasis; Nature Publishing Group; 2006; p. 847-853.
Larsen, T. et al; PPARgamma agonists in the treatment of type II diabetes; ; Intnl. Journal of Obesity; Feb. 2003; p. 147-161, vol. 27, No. 2.
Montague, C. et al; Depot-Related Gene Expression in Human Subcutaneous and Omental Adipocytes; Diabetes; Sep. 1998; p. 1384-1391, vol. 47.
Avram, A. et al:; Subcutaneous fate in normal and diseased states; J. Am. Aca. Dermatol.; Oct. 2005; p. 671-683; vol. 53, No. 4.
Muller, Y. et al.; A Functional Variant in the Perocisame Proliferator; Diabetes, Jul. 2003; p. 1864-1871, Vol. 52.
Hexsel, D. et al.; Botanical Extracts Used int he Treatment of Cellulite; Dermatol Surg.; Jul. 2005; p. 866-872, vol. 31:7 Part 2.

(Continued)

*Primary Examiner*—Robert A Wax
*Assistant Examiner*—Bethany Barham
(74) *Attorney, Agent, or Firm*—Charles J. Zeller; Jean M. McGillycuddy; Anthony M. Santini

(57) ABSTRACT

The present invention is a method of treating skin or hair conditions, such as acne, blemishes, breakouts, cellulite, oily skin, oily hair, oily scalp, or any combination thereof, that comprises topically applying an effective amount of perilla oil to the affected area of the skin or hair. The topical application of perilla oil inhibits PPAR upregulation in skin cells, particularly PPARalpha upregulation.

15 Claims, 2 Drawing Sheets

OTHER PUBLICATIONS

Semple, R. et al.; PPARy and human metabotic disease; J. of Clinical Investigation; Mar. 2006, p. 581-589, Vo. 116, No. 3.

Avram, M; Cellulite: a review of its physiology and treatment; J. Cosmet. Laser Ther.; 2004; p. 181-185, Vo. 6.

Giusti, V. et al.; Expression of Peroxisome Proliferator; Diabetes; Jul. 2003; p. 1673-1676, vol. 52, No. 7.

Mori, Y., et al.; Effect of Troglitazone on Body Fat Distribution in Type 2 Diabetic Patients; Diabetes Care, Jun. 1999; p. 908-912, Vo. 22, No. 6.

Vidal-Puig, A. et al.; Peroxisome Proliferator-activated Receptor Gene Expression in Human Tissues; J. Clin. Invest.; May 1997, p. 2416-2422, vol. 99, No. 10.

Tsai, Y. et al.; Hypertesnion and abnormal fat distribution but not insulin resistance in mice; J. of Clinical Investigation; Jul. 2004, p. 240-249, Vo. 114, No. 2.

Rawlings, A.; Cellulite and its treatment; J. of Cosmetic Science; 2006; p. 175-190, vol. 28.

Birnbaum, L.; Addition of Conjugated Linoleic Acid to a Herbal Anticellulite Pill; Advances in Natural Therapy; Sep./Oct. 2001, p. 225-229, vol. 18, No. 5.

Bertin, C. et al.; A double-bind evaluation of the activity of an anti-cellulite product; J. Cosmet. Sci; Jul./Aug. 2001, p. 199-210, vol. 52, No. 4.

Rao, J. et al., A two-center, double-blinded, randomized trial testing the tolerability and efficacy; J. of Cosm. Derm., 2005, p. 93-102, vol. 4.

* cited by examiner

METHOD OF TREATING SKIN CONDITIONS

BACKGROUND OF THE INVENTION

1. Field of the Invention

The present invention relates to topical compositions and methods useful to prevent, ameliorate or treat skin and other conditions associated with upregulation of genes in skin cells that respond to activation of Peroxisome Proliferator Activated Receptors (hereinafter "PPAR"), which are proteinaceous. More particularly, the present invention relates to topical compositions and methods useful to prevent, ameliorate or treat conditions, such as acne and/or cellulite, associated with upregulation of PPAR.

2. Description of the Related Art

Although the role of PPAR in metabolic pathways is still under investigation, it is known that PPAR receptors have a fundamental role in regulating energy balance, particularly via glucose and lipid metabolism. In addition, it is known that there is not a single PPAR but, instead, a family, or isoforms, of PPAR: PPARalpha, PPARgamma and PPARbeta/sigma.

U.S. Pat. No. 6,004,741 to Rosenfield discusses PPAR in sebocyte development, and suggests that PPAR, particularly PPARgamma, may be useful with respect to conditions associated with increased sebum production, such as acne vulgaris. In addition, U.S. Pat. Nos. 5,994,554 to Kliewer et al.; 5,939,442 to Evans et al.; and 5,981,586 to Pershadsingh, disclose methods to either identify compounds that interact with or modify PPARgamma mediated pathways.

It has been reported that feeding perilla oil to rats reduces visceral adipose tissue by down-regulating adipose cell/tissue differentiation. Okuno et al. J. Nutr. 127: 1752-1757 (1997). Another study in which Japanese Quails were fed perilla oil demonstrated a reduction in plasma lipid levels and foam cells in the aorta. Reducing both plasma lipid levels and aortic foam cells reduces atherosclerosis.

As can be understood by those in the art, compositions that require systemic administration are particularly undesired when treating skin conditions. This is simply because systemic administration provides greater opportunity for an active to interact at receptor sites away from the target site. Non-target receptor activity results in undesired side effects.

U.S. Pat. No. 5,312,834 to Yeo teaches compositions for the treatment of acne. The Yeo patent exemplifies topical compositions having both eicosapentaenoic acid and alpha-linolenic acid, preferably in a weight ratio of 1:0.1 to 20, respectively. Although Yeo teaches that perilla oil contains alpha-linolenic acid and fish oil contains eicosapentaenoic acid, Yeo fails to teach or suggest that perilla oil would be effective to treat acne, absent the required ratio of eicosapentaenoic acid to alpha-linolenic acid.

U.S. Pat. No. 5,997,852 to Yoneda et al. provides an oral remedy for dermatitis that comprises both a zinc compound and a compound that may be either a multivalent unsaturated fatty acid or an ester thereof. Example 8 of the Yoneda et al. patent teaches a formulation comprising zinc sulfate and perilla oil as a source of linoleic acid. However, the Yoneda et al. patent fails to suggest that perilla oil is an effective topically active ingredient to prevent, ameliorate or treat acne or a non-diseased state, i.e. cosmetic, skin condition.

Thus, the prior art fails to disclose or suggest the use of topical compositions having perilla oil in an amount effective to improve the cosmetic appearance of skin by preventing, ameliorating or treating acne and/or non-disease state skin conditions, such as cellulite, that are associated with upregulation of PPAR mediated pathways.

SUMMARY OF THE INVENTION

It is an object of the present invention to provide a method of preventing, treating or ameliorating an affected area of the skin or hair.

It is another object of the present invention to provide a method of improving the aesthetic appearance of an affected, but non-disease state, area of the skin or hair that exhibits characteristics associated with conditions, such as blemishes, skin breakouts, cellulite, oily skin, oily hair, oily scalp, and combinations thereof.

It is yet another object of the present invention to provide a method of treating a skin or hair condition resulting from or accompanied by an upregulation of PPAR receptors.

The present invention, in brief summary, is topical compositions having at least one PPAR Stabilizer, and methods of administering such topical compositions to improve the condition and aesthetic appearance of such affected skin and/or hair.

DETAILED DESCRIPTION OF THE INVENTION

Figure 1:
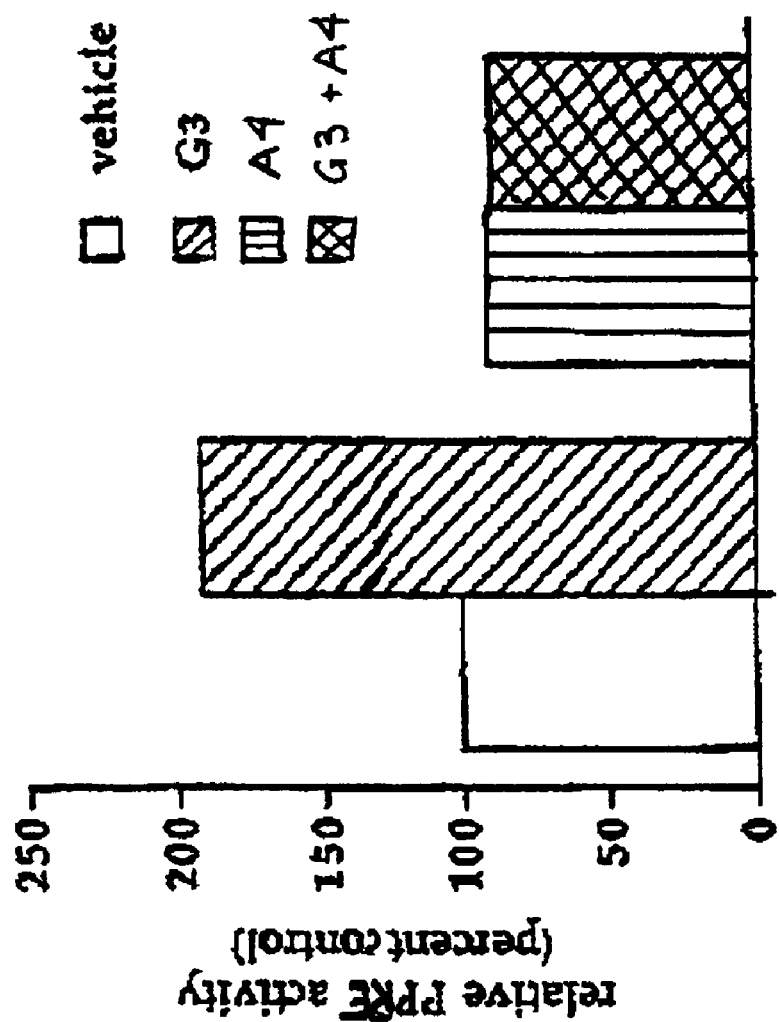
FIG. 1 illustrates the results of Example 1.

A "topical composition" as used herein refers to a composition intended to be directly applied or spread on the surface of skin and/or hair and scalp. An "effective amount" means an amount of a compound or a composition sufficient to induce a positive change in the skin and/or hair condition. A "physiologically acceptable vehicle" or a "suitable topical vehicle" refers to a cosmetic, medicament or inert ingredient that is suitable for use in direct contact with human tissues without undue toxicity. All percentages refer to weight percent based on the total weight of the topical composition.

The first principal component of the present invention is an inhibitor of PPAR upregulation (hereinafter "PPAR Stabilizer"). The term PPAR Stabilizer as used herein encompasses all compounds that inhibit upregulation of genes that respond to activation of PPAR proteins via agonists, but do not effect basal levels of PPAR activity. In other words, the PPAR Stabilizer competes with the agonist that upregulates PPAR activity. The differentiation between upregulated and normal PPAR activity will be discussed below.

The preferred PPAR Stabilizer is perilla oil, especially perilla seed oil. Perilla seed oil contains a highly unsaturated drying oil similar to linseed oil. It is surprising and unexpected that perilla oil inhibits upregulation by PPAR agonists, as perilla oil itself contains PPAR agonists such as linolenic acid and linoleic acid. This may be attributable to perilla oil undergoing oxidation on storage due to the high content of unsaturated fatty acids. The oxidation process may alter the PPAR stimulating activity of linolenic acid and linoleic acid, causing the acids to bind to and shield the receptors, but not activate them, thereby preventing other agonists from reaching and activating the receptors.

In addition to the PPAR Stabilizer, the present invention may include a secondary component. The secondary component is selected from one or more of the following eleven groups.

1. Retinoids and Rexinoids: Examples of suitable retinoids include retinol, retinoic acid, retinyl palmitate, retinyl propionate, retinyl acetate, isotretinoin as well as synthetic retinoid mimics, and derivatives of the foregoing, as well as others that bind to RAR receptors. Rexinoids include compounds, such as all-trans retinoic acid, 9-cis retinoic acid, phytanic acid and others that bind to RXR receptors.

2. An estrogen synthetase (aromatase) stimulating compound: Examples of such a compound include caffeine and/or derivatives thereof, and any mixture thereof. Caffeine is the more preferred of such compounds.

3. A compound capable of inhibiting 5 alpha-reductase activity: Examples of such a compound include linolenic acid, linoleic acid, finasteride, and mixtures thereof.

4. An exfoliation promoting compound: Suitable examples include alpha hydroxy acids; beta hydroxy acids; oxa acids as disclosed in U.S. Pat. No. 5,847,003 (the disclosure of which is incorporated herein by reference); oxa diacids as disclosed in U.S. Pat. No. 5,834,513 (the disclosure of which is incorporated herein by reference); mechanical exfoliation compounds, such as bamboo exfoliant extract; salicylic acid; benzoyl peroxide; keto acids, such as pyruvic acid, 2-oxopropanoic acid, 2-oxobutanoic acid, and 2-oxopentanoic acid; and mixtures thereof.

The preferred exfoliation promoting compounds are lactic acid, glycolic acid, 3,6,9-trioxaundecanedioic acid, and any mixture thereof. When the present invention includes an exfoliation promoting compound, the composition comprises about 1 wt % to 20 wt %, preferably about 1 wt % to about 15 wt %, more preferably about 4 wt % to about 10 wt % acid, and most preferably about 4 wt % of the exfoliation promoting compound.

5. An ultraviolet (UV) light protecting/sunscreen agent: Examples include organic and inorganic sunscreens, such as titanium dioxide, zinc oxide, methyl benzylidene camphor and/or its derivatives, octocrylene, anthranilates, benzophenones, butylmethoxydibenzoylmethane (avobenzone), naphtholsulphonates, benzoic acid derivatives, salicylates, cinnamic acid derivatives, terephthalylidene dicamphor sulfonic acids, and mixtures thereof. Of these, butylmethoxydibenzoylmethane, octocrylene, octylsalicylate, octylmethoxycinnamate and oxybenzone, and mixtures thereof are preferred. Butylmethoxydibenzoylmethane, oxybenzone, octylmethoxycinnamate, terephthalylidene dicamphor sulfonic acids, and mixtures thereof are most preferred. Salts, esters and other derivatives of the aforementioned sunscreen agents, which are compatible with the composition, are also contemplated in practicing the present invention. Co-formulation with an ultraviolet light protecting/sunscreen agent is particularly desirable when the present invention is prepared for consumers who engage in outdoor activities.

6. Barrier function enhancing agents: Examples include ceramides; essential fatty acids and their esters, especially glycerides, α-hydroxy fatty acids and their esters, w-hydroxy fatty acids and their esters; phospholipids; cholesterol and its esters, such as cholesteryl hemisuccinate, cholesteryl phosphate; and cholestanol and its derivatives. The barrier function enhancing agent can be added to a topical composition either as singular molecular entities or as a complex mixture of lipids derived from either synthetic, animal or plant sources.

7. Collagen enhancing agents: These agents prevent skin sagging by promoting a net increase in collagen, either by reducing collagen breakdown or by promoting collagen formation. Examples of such agents include *Clara* extract (*Sophora augustifolia*), ascorbyl-phosphoryl-cholesterol, ascorbic acid, ascorbic acid derivatives, and mixtures thereof.

8. Elastase inhibitors: Examples of these inhibitors include fatty acids, such as oleic acid, perinaric acid, and Honeysuckle extract (*Lonicera caprifolium*). These inhibitors act to prevent sagging of the skin.

9. Skin lightening agents: Examples include kojic acid, hydroquinone, licorice derivatives, ascorbic acid/ascorbic acid derivatives (e.g. magnesium ascorbyl phosphate), arbutin, bearberry (*Arctostaphylos uva ursi*), *Glycyrrhiza glabra* and its derivatives, *Chlorella vulgaris* extract, and mixtures thereof.

10. Antioxidants: Examples include compounds having phenolic hydroxy functions, such as ascorbic acid, ascorbic acid derivatives, gallic acid derivatives (e.g. propyl gallate); ferulic acid derivatives (e.g. ethyl ferulate, sodium ferulate); nitrones; N-tertbutyl-nitrone; I-(4-pyridyl-1-oxide)-N-tert-butyl-nitrone; curcumin, tetrahydrocurcumin; 6-hydroxy-2,5,7,tetramethylchroman-2-carboxylic acid; uric acid; reductic acid; tannic acid; rosmarinic acid; tocopherol and its derivatives; catechins; and mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as sulfites, bisulfites, metabisulfite, or other inorganic salts and acids containing sulfur.

11. Skin warming agents: Examples include vanillyl butylamid, capsaicin and mixtures thereof.

The secondary component enhances the dermatological benefits achieved by the PPAR Stabilizer. The compositions of the present invention may include at least two secondary components, with each secondary component being selected from a different group.

The compositions of the present invention can include other cosmetic and pharmaceutical actives and excipients. Such suitable cosmetic and pharmaceutical agents include, but are not limited to, one or more of erythromycins, tetracyclines, salicylic acids, antifungals, vitamins, anti-inflammatory agents, antimicrobials, analgesics, nitric oxide synthase inhibitors, insect repellents, self-tanning agents, surfactants, moisturizers, stabilizers, preservatives, antiseptics, chelating agents, thickeners, emulsifiers, lubricants, humectants, chelating agents, skin penetration enhancers, skin cooling agents, emollients, fragrances and colorants.

Examples of suitable thickening agents include xanthan gum, hydroxypropyl cellulose, hydroxyethyl cellulose, carbomer, gum acacia, Seppigel 305 (available from Seppic Co., France), and magnesium aluminum silicate.

The topical compositions of the present invention can include, and their utility can be enhanced by, one or more of humectants, such as ureas, pyrrolidone carboxylic acids, amino acids, sodium hyaluronates, certain polyols and other compounds with hygroscopic properties.

The general activity and mildness to skin of the present topical compositions can also be enhanced by neutralization to pH about 3.5 to about 7.0, most preferably from pH about 3.7 to about 5.6. This neutralization is preferably accomplished with one or more of ammonium hydroxide, potassium hydroxide, sodium hydroxide, arginine or other amino acids, and/or triethanolamine.

The topical compositions of the present invention can be further formulated according to procedures known in the art to provide cosmetic compositions such as emulsions, gels, creams, lotions, ointments, pastes, sticks, cakes, pencils, essences and serums, as well as other topical cosmetic vehicles. It is also contemplated that topical compositions of the present invention can be incorporated into delivery systems such as liposomes and topical patches, tapes, and sprays.

PPAR Stabilizers

The topical compositions of the present invention are useful to improve the aesthetic appearance of skin, particularly teen skin, by any one of the following methods:
1. Reducing oil production by sebaceous glands;
2. Reducing lipid synthesis in subcutaneous adipose tissue;
3. Reducing triglyceride synthesis in subcutaneous adipose tissue;
4. Preventing and/or improving skin conditions associated with nonselective or partially selective PPAR stimulators/upregulators;
5. Preventing, ameliorating or treating acne;
6. Preventing, ameliorating or treating oily skin;
7. Preventing, ameliorating or treating oily hair;
8. Preventing, ameliorating or treating oily scalp;
9. Preventing, ameliorating or treating cellulite; and
10. Preventing, ameliorating or treating blemishes;
11. Preventing, ameliorating or treating breakouts; and
12. Improving skin texture.

The foregoing methods are achieved by topically applying an effective amount of a PPAR Stabilizer in a topical composition, to affected areas. Preferably the PPAR Stabilizer is perilla oil and, more preferably, the perilla oil is derived from the perilla seed, i.e. perilla seed oil.

As discussed above, the discovery that perilla oil is useful as a PPAR stabilizer is an unexpected discovery in light of the prior art. It is very surprising that perilla oil as a source of linolenic acid and linoleic acid (known non-selective PPAR agonists) can prevent upregulation of PPAR, thereby providing a positive effect on acne and cellulite.

When the PPAR Stabilizer is perilla oil, the PPAR Stabilizer may be directly applied to the affected area. It is preferred that the PPAR Stabilizer is incorporated into a topical composition in an amount from about 0.01 wt % to about 10 wt %. More preferably, the PPAR Stabilizer is incorporated into the topical composition in an amount from about 1 wt % to about 8 wt %. It is most preferred that the PPAR Stabilizer is incorporated into the topical composition in an amount from about 3 wt % to about 6 wt %.

As can be understood by those in the art, the number of applications per day may vary upon the concentration of PPAR Stabilizer in the topical composition, as well as the nature of the vehicle of the topical composition, such as a gel versus a topically applied patch. When the topical composition has from about 0.01 wt % to about 10 wt % perilla oil in a cream vehicle, it is believed that such a composition should, preferably, be applied one to three times a day for acne conditions and one to two times a day for cellulite conditions. When such a topical composition is used to improve the overall aesthetic appearance of skin, it is preferred that the topical composition is applied one to two times a day.

When the condition to be treated is cellulite located on the thigh, the topical composition should be applied directly on the area. When the condition to be treated is oily scalp, the topical composition may be in the form of a shampoo or conditioner. When the condition is oily hair, the topical composition may additionally be in the form of a styling gel, hair spray or leave-in conditioner.

When the condition to be treated is acne, the composition may include: perilla oil having alpha-linolenic acid, eicosapentaenoic acid, and a suitable vehicle. However, it is preferred that the weight ratio of eicosapentaenoic acid to alpha-linolenic acid is outside the range of 1:0.1 to 20. Fish oil is a known and suitable source of eicosapentaenoic acid. When fish oil is the source of eicosapentaenoic acid, it is preferred that the fish oil includes less than 5 wt % or greater than 40 wt % eicosapentaenoic acid and the perilla oil includes less than 30 wt % or greater than 70 wt % of alpha-linolenic acid. Also, it is preferred that the volume of fish oil in the composition is either less than one-tenth the volume of perilla oil in the composition or greater than ten times the volume of perilla oil in the composition.

The following examples are illustrative of the present invention and are not intended to limit the invention.

EXAMPLE 1

Human skin cells were used to determine the effect upon PPAR upregulation by known PPAR agonists and the compound of the present invention as measured by relative PPRE ("Peroxisome Proliferator Response Element") activity. Preconfluent keratinocytes were transiently transfected with a PPRE-luciferase reporter construct together with a beta-galactosidase. Four similar groups of cells were treated the following day for 24 hours. The first group contained a vehicle having 0.05% dimethyl sulfoxide (DMSO). The second group was treated with G3, a PPAR alpha agonist. The third group was treated with A4, perilla seed oil diluted 1:100 with DMSO. The fourth group was treated with G3 and A4.

As the results illustrated in FIG. 1 show, the addition of a PPAR agonist (G3) nearly doubled the PPRE activity as compared to the vehicle. The addition of perilla seed oil (A4) completely prevented the upregulation of PPAR in the presence of G3.

EXAMPLE 2

Figure 2:
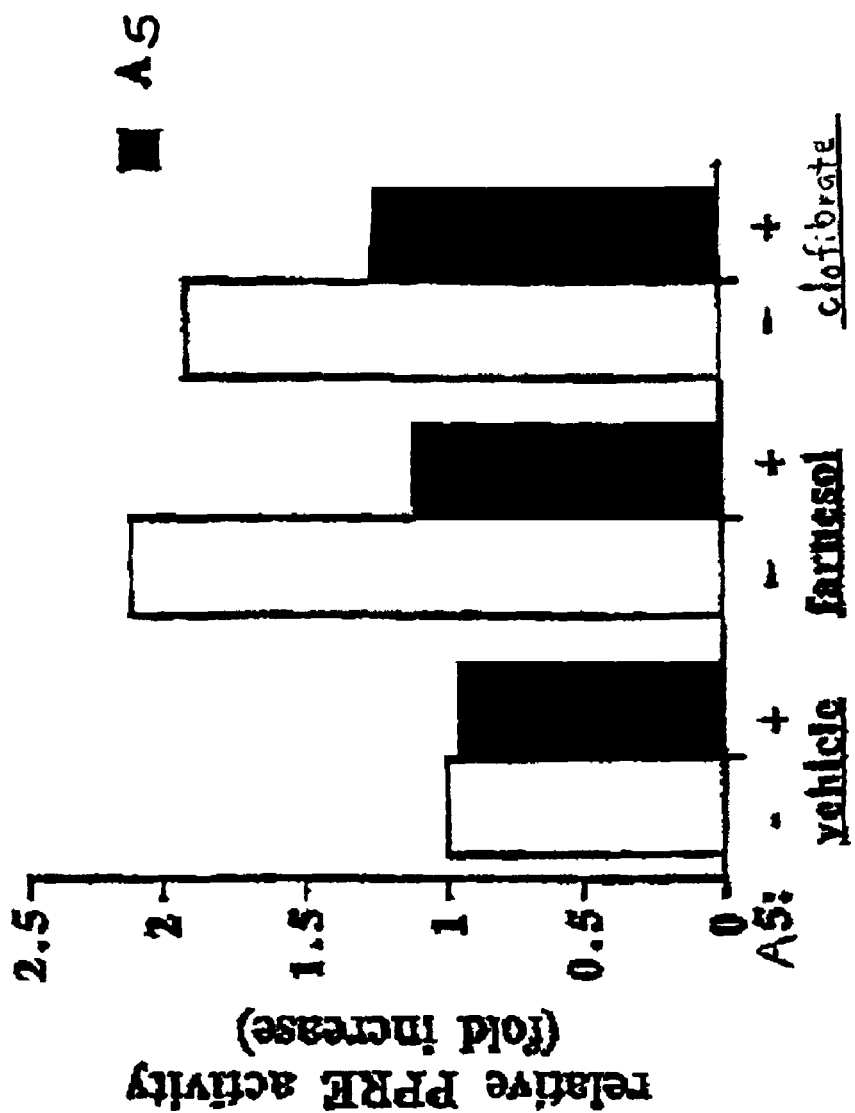
FIG. 2 illustrates the results of Example 2.

As in Example 1, preconfluent keratinocytes were transfected with PPRE-luciferase and beta-galactosidase. Six similar groups of cells were treated the following day for 24 hours. The first group contained a vehicle having 0.05% DMSO. The second group was treated with A5, perilla seed oil diluted 1:100 with DMSO. The third group was treated with farnesol, a PPAR activator. The fourth group was treated with farnesol and A5. The fifth group was treated with an analog of clofibrate, a known PPAR alpha agonist. The sixth group was treated with the clofibrate analog and A5. As the results illustrated in FIG. 2 show, the addition of A5 to cells treated with the PPAR agonists significantly prevents PPAR upregulation. In fact, even in the presence of such agonists, A5 maintains PPRE activity in the range exhibited by the vehicle alone.

Various modifications and alterations to the present invention may be appreciated based on a review of this application. These changes and additions are intended to be within the scope and the spirit of the present invention as defined by the following claims.

What is claimed is:

1. A method of ameliorating or treating cellulite, comprising topically applying a composition comprising from about 0.01 wt % to about 10 wt % perilla oil to an area of skin affected by cellulite.

2. The method of claim 1, wherein the composition comprises from about 1 wt % to about 8 wt % perilla oil based on the total weight of the topical composition.

3. The method of claim 1, wherein the composition comprises from about 3 wt % to about 6 wt % perilla oil based on the total weight of the topical composition.

4. The method of claim 1, wherein the perilla oil is perilla seed oil.

5. The method of claim 2, wherein the perilla oil is perilla seed oil.

6. The method of claim 3, wherein the perilla oil is perilla seed oil.

7. The method of claim 1, wherein the perilla oil is topically applied one or two times per day.

8. The method of claim 2, wherein the perilla seed oil is topically applied one or two times per day.

9. The method of claim 3, wherein the perilla seed oil is topically applied one or two times per day.

10. The method of claim 4, wherein the perilla seed oil is topically applied one or two times per day.

11. The method of claim 5, wherein the perilla seed oil is topically applied one or two times per day.

12. The method of claim 6, wherein the perilla seed oil is topically applied one or two times per day.

13. The method of claim 1, wherein the composition comprises from about 1 wt % to about 3 wt % perilla oil based on the total weight of the topical composition.

14. The method of claim 13, wherein the perilla oil is perilla seed oil.

15. The method of claim 14, wherein the perilla seed oil is topically applied one or two times per day.

\* \* \* \* \*